(12) United States Patent
Carr

(10) Patent No.: US 6,420,185 B1
(45) Date of Patent: Jul. 16, 2002

(54) WATER CONTAMINATION CONCENTRATION APPARATUS AND PROCESS

(75) Inventor: Gregory E. Carr, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/408,188

(22) Filed: Sep. 28, 1999

(51) Int. Cl.[7] ................................................. G01N 1/34
(52) U.S. Cl. ..................... 436/177; 73/61.41; 73/61.42; 73/61.59; 73/863.23; 210/650; 210/652; 210/900; 422/101; 436/178
(58) Field of Search ................................ 422/68.1, 101; 436/177, 178; 73/61.41, 61.42, 61.59, 863.23; 210/650, 652, 900

(56) References Cited

U.S. PATENT DOCUMENTS 5,160,044 A * 11/1992 Tan
5,252,350 A * 10/1993 Hartmann
6,051,189 A * 4/2000 Wick et al.

* cited by examiner

Primary Examiner—Jan Ludlow
(74) Attorney, Agent, or Firm—Robert G. Winkle

(57) ABSTRACT

An apparatus and methods of utilizing a semi-permeable membrane to concentrate contaminants in a portion of an Ultra Pure Water stream to levels which are detectable by an on-line analyzer. This allows the use of analyzers that would not be able to accurately detect contaminant concentrations in the Ultra Pure Water stream. Thus, by knowing the concentration factor and the level of contaminants in the concentrated stream indicated by the analyzer the real level of contamination can be back calculated.

4 Claims, 10 Drawing Sheets

WATER CONTAMINATION CONCENTRATION APPARATUS AND PROCESS

BACKGROUND OF THE INVENTION

1. Field of the Invention

The present invention relates to methods for testing water for contaminants. In particular, the present invention relates to utilizing a contaminant concentration process for on-line contaminant testing of a continuous ultra pure water stream.

2. State of the Art

Ultra pure water (hereinafter "UPW") is, simply, water with extremely low concentrations of contaminating materials. Such low contaminant concentrations make UPW a very efficient solvent. Thus, it is used in a wide range of industries including food processing and microelectronic device fabrication for cleaning products and process equipment without leaving behind contaminants that can adversely affect product quality. UPW is also used in biological processes, medical facilities, and pharmaceutical manufacturing which impose special purity requirements. UPW can be produced by a variety of techniques known in the art, but is primarily produced using dead-end filtration with polymeric membranes.

In the microelectronics industry, the use of UPW is critical, because active ions and solid particles in process water can result in the alteration of the current carrying characteristics of microelectronic devices by causing insulation breakdown and electrical shorts. In semiconductor devices, even minute particles less than a micron in size are able to destroy an entire wafer of semiconductor chips. Furthermore, even if a microelectronic device is not immediately destroyed by impurities, the impurities may affect the long-term reliability of the device.

With such a dramatic impact on device production, the microelectronics industry is continuously working toward making UPW even cleaner. However, water-purifying techniques for producing UPW have been improving more rapidly than the technology of on-line contaminant analyzers. In other words, UPW has become so clean that the ability to accurately test for contaminants on-line has become almost impossible. For example, current levels of individual contaminants, such as silica, metals, most anions and cations, and sodium, are in the parts per billion, even as low as parts per trillion. These levels are far below the existing lower detection limits of even the highest quality on-line analyzers.

Furthermore, an analyzer does not output the true contaminant level, because they also output a "zero" level created by the inherent signal noise of the analyzer. Thus, the contaminants concentration can become so low that the "zero" level begins to give false readings. Such erroneous data is very detrimental because knowing the true level of specific contaminants is crucial for the application of statistical process control monitoring techniques and true process alarming. Thus, water quality cannot be effectively monitored to prevent compromises in UPW quality before critical levels are reached.

Although laboratory analysis does have the capability to measure contaminants at the parts per billion and parts per trillion levels, the turn-around time from water sampling to assessment is far too long for real time monitoring.

Therefore, it would be advantageous to develop apparatus and techniques for on-line UPW testing to accurately measure and monitor minute levels of contaminants utilizing commercially available water purification equipment.

SUMMARY OF THE INVENTION

A contamination concentration device including a filtering device, which is feed a feed stream (containing a contaminant of interest) and which separates the feed stream into a product stream and a concentrate stream. The contamination concentration device further includes a contaminant analyzer which is feed the concentrate stream and which analyzes the concentration of the contaminant of interest in the concentrate stream. In general, the concentrate stream contains a higher concentration of the contaminant of interest than the feed stream.

The contamination concentration device is utilized by delivering the feed stream to the filtering device and separating the feed stream into the product stream and the concentrate stream. The concentrate stream is then delivered to the contaminant analyzer, which determines the concentration of the contaminant of interest within the concentrate stream. Using the determined concentration of the contaminant of interest, a concentration of the contaminant of interest within the feed stream is determined.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE ILLUSTRATED EMBODIMENT

Although FIGS. 1, 2, 9 and 10 illustrate various views of the present invention, these figures are not meant to portray any water treatment or analysis equipment in precise detail.

Rather, these figures illustrate such equipment in a manner to more clearly convey the concepts of the present invention. Additionally, elements common between the figures retain the same numeric designation.

Figure 1:
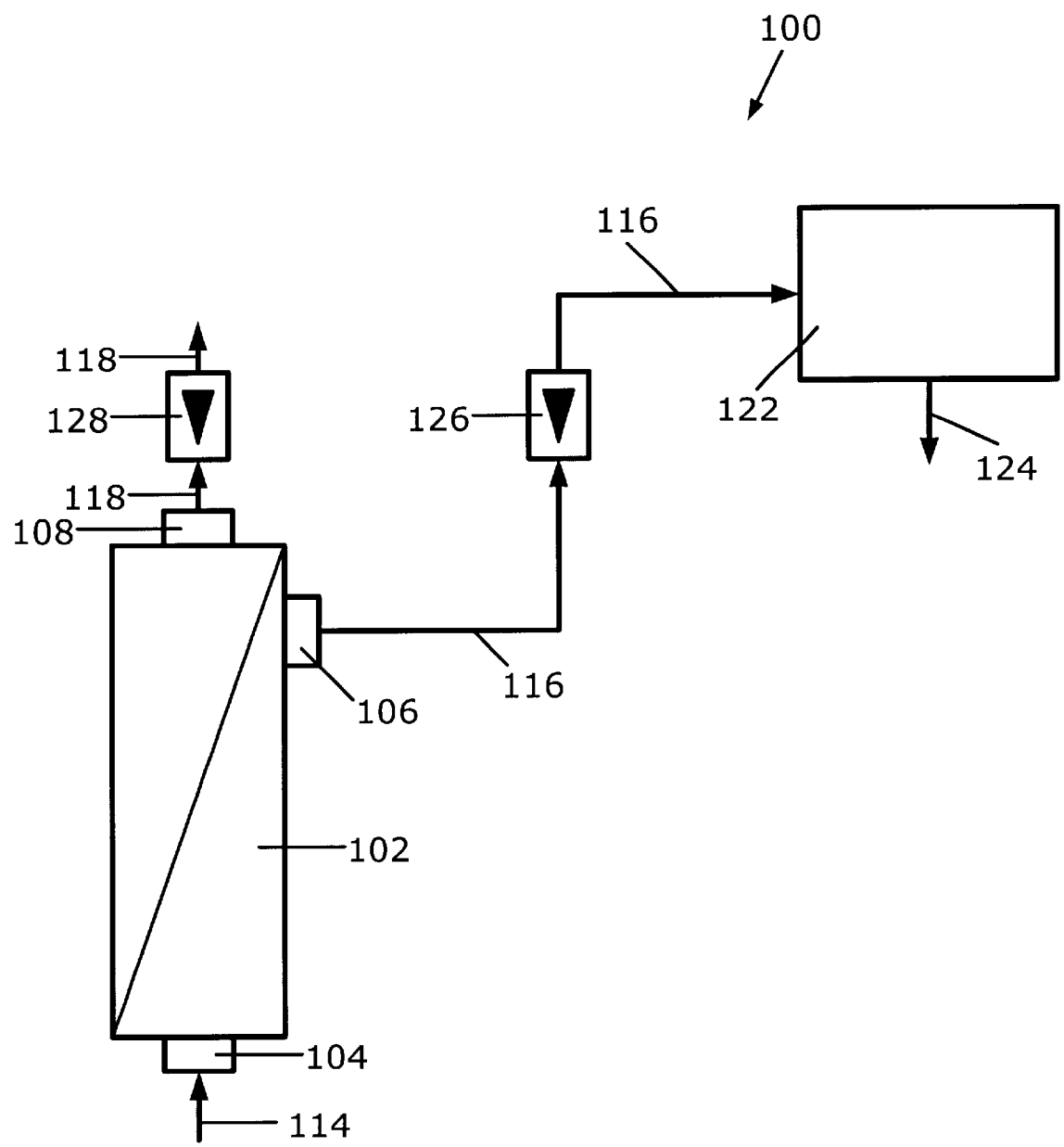
FIG. 1 is a schematic of a water contamination concentration apparatus, according to the present invention.

FIG. 1 illustrates an embodiment of a contaminant concentration apparatus 100 according to the present invention. The contaminant concentration apparatus 100 comprises a filtering unit 102 having a feed stream inlet 104, a concentrate stream outlet 106, and a product stream outlet 108. The filtering unit 102 is preferably a semi-permeable membrane-type system, including but not limited to reverse osmosis, nanofiltration, and ultrafiltration systems, as known in the art.

A feed stream 114 potentially containing the contaminant(s) of interest enters the feed stream inlet 104. The feed stream 114 is a portion of a UPW stream (not shown) used in a fabrication process. The filtering unit 102 separates the feed stream 114 into a concentrate stream 116 containing the contaminant(s) of interest in a concentrated form, which exits through the concentrate stream outlet 106, and a product stream 118, which exits through the product stream outlet 108. The concentrate stream 116 feeds an analyzer 122, which determines the concentration of the contaminant(s) of interest in the concentrate stream 116 and expels the analyzed concentrate stream as a waste stream 124. The concentration of the contaminant(s) of interest in the feed stream 114 is then calculated based on the concentration of the contaminant(s) of interest in the concentrate stream 116, the flow rate of the concentrate stream 116 as determined by a concentrate stream flowmeter 126, and the flow rate of the product stream 118 as determined by a product stream flowmeter 128. This calculation will be discussed in further detail below. The analyzer 122 may be either a continuous analysis or a grab sample-type analysis system. It is, of course, understood that flowmeters on any two of the feed stream 114, the concentrate stream 116, and the product stream 118 can be used for the water balance information needed to calculated the contaminant concentrate in the feed stream 114.

The concentration of the contaminant(s) of interest in the concentrate stream 116 is a function of the flow ratio between the feed stream 114 and the concentrate stream 116 (hereinafter "the concentration ratio"). However, the concentration function varies with each specific contaminant of interest (i.e., how well a specific contaminant of interest can be separated from a feed stream for a given equipment configuration). Thus, this must be preestablished by laboratory analysis for each specific contaminant of interest. The concentration ratio can be varied by simply varying the flow ratio between the feed stream 114 and the concentrate stream 116. The variable concentration ratio is useful for matching the sample concentration to the analytical capabilities of the analyzer 122 to provide a stable and accurate analysis. Additionally, the product stream 118 is actually purified cleaner than the feed stream 114, and is thus suitable for immediate re-use without waste. Furthermore, the technique of the present invention uses no energy or chemicals.

Therefore, the technique of the present invention overcomes the detection limits of existing analyzers by increasing the contaminant concentration before analysis is attempted. For example, a silica analyzer may have a lower detection limit of 0.2 micrograms per liter. If the contaminants in a sample of water are concentrated by a factor of 100, then the functional detection limit is lowered to 0.002 micrograms per liter using the same analytical instrumentation.

EXAMPLE 1

Figure 2:
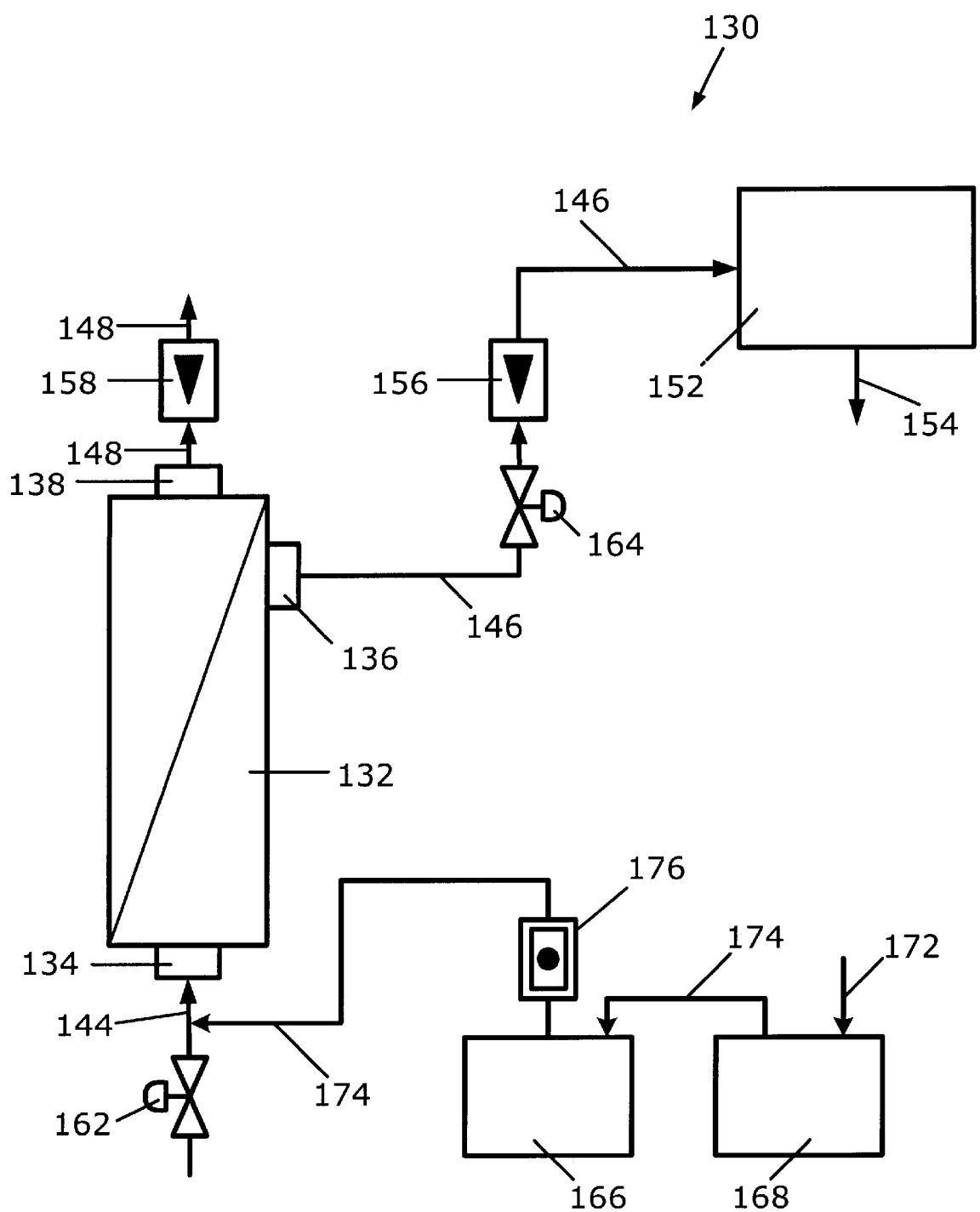
FIG. 2 is a schematic of a water contamination concentration apparatus having a silica standard stream delivered to the feed stream of the apparatus, according to the present invention.

FIG. 2 illustrates an experimental contaminant concentration apparatus 130 according to the present invention. A continuous flow of UPW, denoted as feed stream 144. was fed through feed stream inlet 134 into a self-contained Reverse Osmosis unit 132 (ESPAFREE 3000 Module, Hydranautics, Oceanside, Calif., USA). Reverse Osmosis (hereinafter "RO") is used to either remove contaminants from the desired product stream, or remove excess water from a desired product. In typical applications, the 'recovery' of the product is usually limited to approximately 15% of the feed water to any single RO element. In other words, if 100 units are fed to the RO unit 132, 15 units exit a product stream outlet 138 as a product stream 148 and 85 units exit a concentrate stream outlet 136 as a concentrate stream 146. However, for the present invention the RO unit 102 is run in a near "dead-end" mode. with the flow of the concentrate stream 146 significantly lower than normal operation. It is believed that recoveries as high as 99.5% are feasible when running in dead-end mode. Thus the flow of the product stream 148 can be 10 to 200 times the flow of the concentrate stream 146. This is a significant difference from known applications of reverse osmosis systems.

A product flowmeter 158 is attached to the product stream 148 and a concentrate flowmeter 156 is attached to the concentrate stream 146. The flow rate of the feed stream 144 was controlled by a feed stream valve 162 and the flow rate of the concentrate stream 146 was controlled by a concentrate stream valve 164. It is, of course, understood that the various flow rates of streams through the contaminant concentration apparatus 130 may controlled by controlling the flows in any two of the feed stream 144, the concentrate stream 146, and the product stream 148.

After determining the concentration ratio of the product stream 148 to the concentrate stream 146. knowing the recovery of the contaminant concentration apparatus 130, and knowing the capability of the analyzer 152, the true level of contaminant in the feed stream 144 can determined. The recovery of the contaminant concentration apparatus 130 and the capability of the analyzer 152 were determined using silica as the test contaminant. Silica was chosen as the test contaminant, because it is a good indicator species of a UPW system as a whole. Silica levels are usually the first to increase if there are any problems during the production of UPW.

A peristaltic pump 166 and pressurized sample bottle 168 (pressurized by a nitrogen gas feed 172) were used to feed a silica standard stream 174 at various flow rates (controlled by flow controller 176) into the feed stream 144. The silica standard stream 174 is thus continuously added into the feed stream 144 (having a known flow rate). Thus this is essentially an on-line equivalent of an unknown-plus standard test traditionally performed off-line in analytical laboratories. By comparing contamination level results from the analyzer 152 and the known amount of silica added in the silica standard stream 174, the recovery of the entire process, including the concentration efficiency of the RO unit 132 and capabilities of the analyzer 152, was determined.

EXAMPLE 2

Identical sets of tests were run on two silica analyzers. a HACH 5000, Hach Company, Loveland, Colo., USA and a Bran+Luebbe, Bran+Luebbe, Norderstedt, Germany, referred to hereinafter as Analyzer A and Analyzer B, respectively. Two silica analyzers were used to ensure reproducibility and accuracy. Additionally, the testing of separate analyzers ensured that the process of the present invention is analyzer independent (i.e., that the general technique will work for more than one type of analyzer). Test runs usually lasted between about three to four hours to ensure analyzer and RO unit stabilization, and generated between about thirty to forty analyzer readings. The same reverse osmosis unit (i.e., ESPAFREE 3000 Module. Hydranautics. Oceanside, Calif., USA) was with Analyzer A and Analyzer B for the tests.

Figure 3:
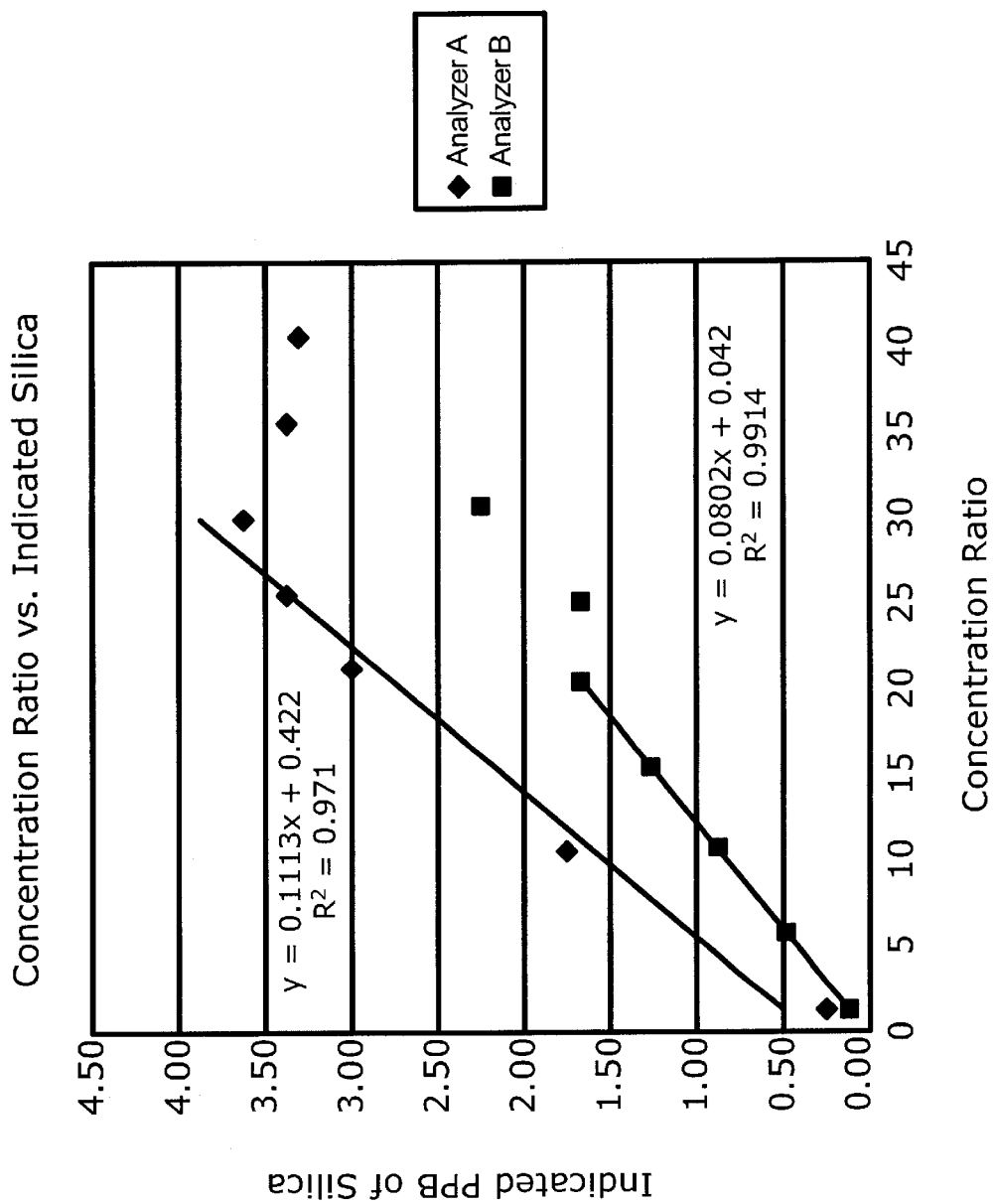
FIG. 3 is a graph of indicated PPB of silica versus the concentration ratio for tests of both Analyzer A and Analyzer B, according to the present invention.

The first set of tests focused on varying the flow of the product stream 148 to vary the concentration ratio between this flow and the flow of the concentrate stream 146 running to the analyzers. FIG. 3 is a graph of the data generated. As expected, the indicated silica concentration in PPB (the y-axis) generally increases as the concentration ratio increases (the x-axis). By increasing the concentration ratio, more silica is measured by the analyzers as it is filtered out by the RO unit 132 into the concentrate stream 146. However, indicated silica concentration readings begin to level off beginning at concentration ratios of about thirty for Analyzer A and about twenty for Analyzer B. The exact cause of this trend at higher ratios is not known at this time. However, up to the "level off" points for each of the analyzers, the data flits a linear trend and indicates that the concentration technique can be utilized up to a concentration ratio of approximately 20. Discrepancies between Analyzer A and Analyzer B in the indicated PPB of silica at the same concentration ratios are most likely due to the greater accuracy and lower zero limit of Analyzer B.

The second sets of tests consisted of the addition of the silica standard stream, as previously discussed. A commercially available 500 $\mu$g/L silica standard (HACH 5000 Silica Standard, Hach Company, Loveland, Colo., USA) was fed, as silica stream 174, to the feed stream 144 with the peristaltic pump 166 injunction with the pressurized sample bottle 168. The silica stream 174 was fed at three different rates of 0.1, 0.3, and 0.5 ml/min., which added 0.5 PPB, 1.5 PPB, and 2.5 PPB of silica, respectively, to the feed stream 144 flowing at 100 ml/min. These additions were completed for each of the four concentration ratios of 5×, 10×, 15×, and 20×. For a control data set, a 1× concentration was also run. The 1× concentration run comprised feeding the feed stream 144 and the silica stream 174 directly to the analyzers without passing the streams through the RO unit 132. Again, test runs on the analyzers lasted for a minimum of about three hours. The readings from both analyzers were very consistent, demonstrating that the standard addition system was able to guarantee consistent single-digit parts per billion standards.

Figure 4:
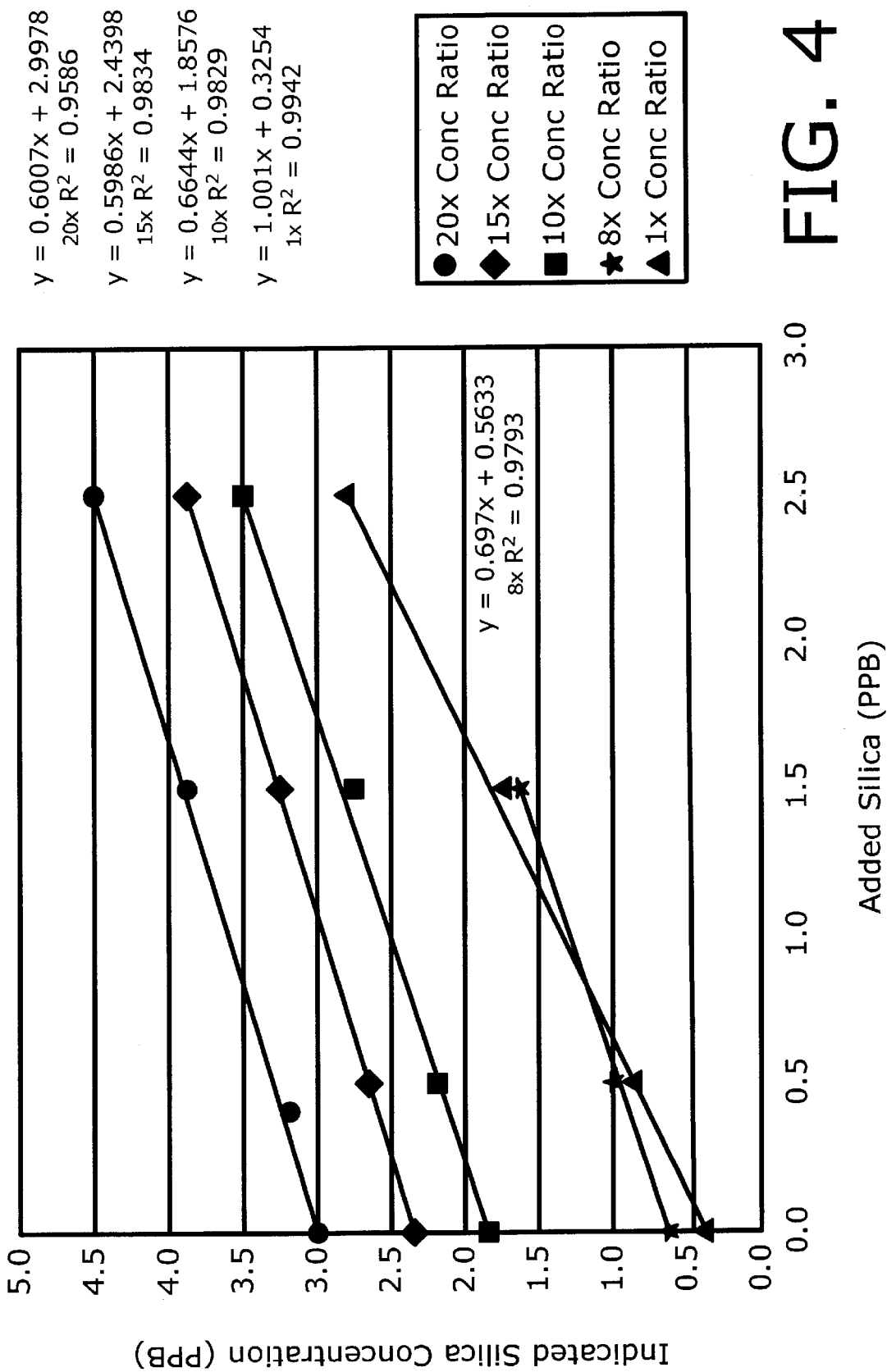
FIG. 4 is a graph of the results added silica standard stream tests with Analyzer A graphed as added silica (PPB) vs. Indicated Silica Concentration (PPB), according to the present invention.
Figure 5:
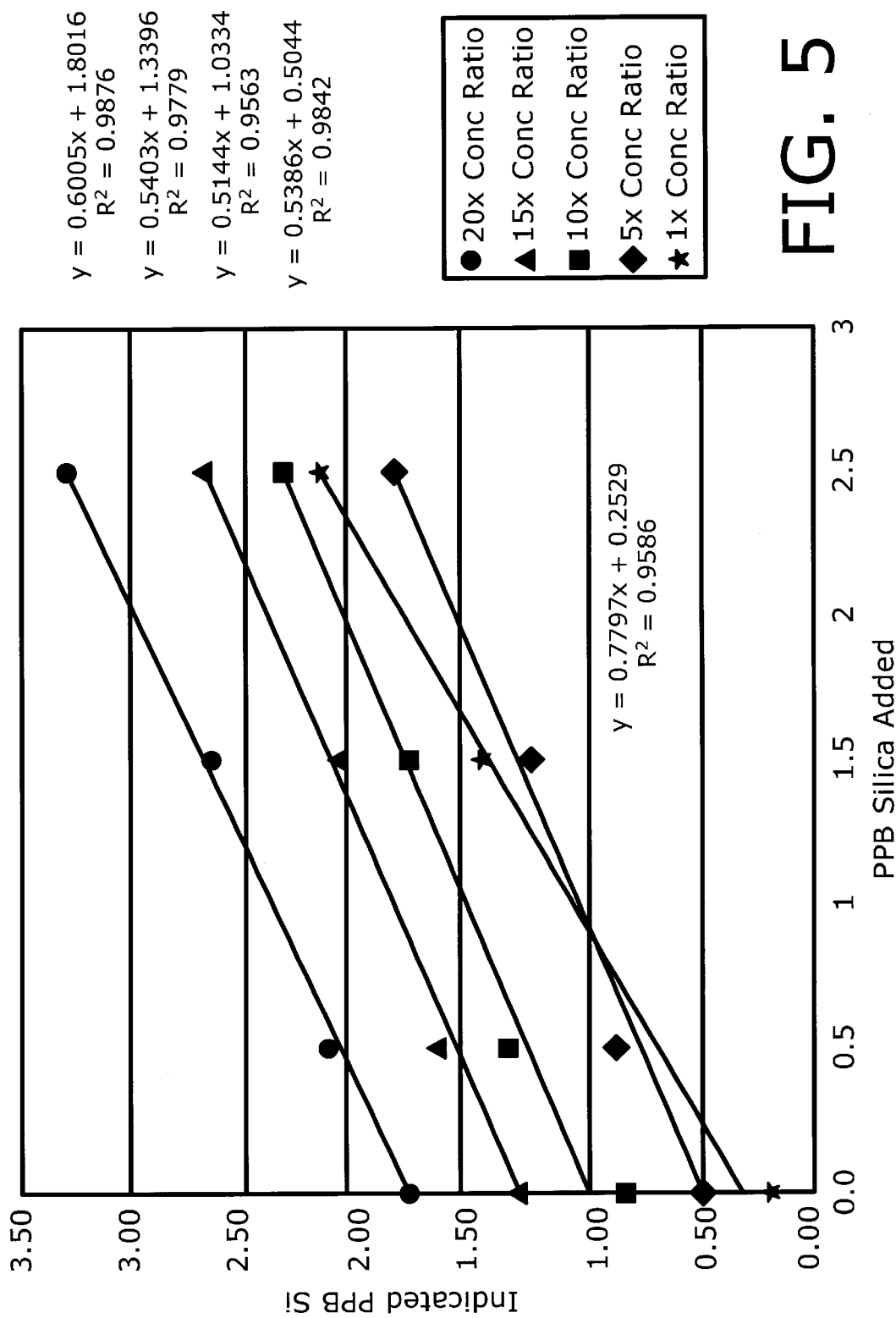
FIG. 5 is a graph of the results added silica standard stream tests with Analyzer B graphed as added silica (PPB) vs. Indicated Silica Concentration (PPB), according to the present invention.

FIG. 4 illustrates the results with Analyzer A and FIG. 5 illustrates the results with Analyzer B. The results are graphed as added silica (PPB) vs. Indicated Silica Concentration (PPB) to easily determine the percent recovery of this UPW concentration technique. If one hundred percent of the silica added with the silica stream 174 was recover and concentrated in the RO unit 132, analyzers readings at the silica standard addition flow rates at 0.5 ml/min. should be 2.5 PPB higher than readings with no silica addition at the same concentration ratio. The slope of the trendline thus indicates the percent recovery and would be equal 1.00 to correspond to the one hundred percent recovery in the theoretical case. This analytical method also eliminates the necessity of determining the unknown silica content in the UPW in order to calculate how much of the silica read by the analyzer originates from silica already present in the UPW and how much originates from the silica standard added.

Again, the data for both analyzers fit linear trends. For all runs, with the exception of the control run, the recovery slopes are similar and the trendlines are to substantially parallel for each analyzer. It was expected that increasing the concentration ratio would significantly decrease the amount of silica recovered, but it appears this is not the case when concentrating at or below the 20× limit determined previously in the first set of tests. Thus, when using the RO concentrator and Analyzer A, the average recovery is about 62% and when using the RO concentrator and the Analyzer B, the average recovery is about 55%.

Another unexpected finding was discovered when comparing the slope of the control run with the slopes of the test runs. It was expected that the slope of the control run would be substantially the same (i.e., parallel) as the slopes of the test runs. However, for both analyzers. the slope of the control run is much steeper than the other test involving the addition of silica standard. It was determined that without the efficiency of the RO element playing a factor, the recovery given by the control run's slope is actually the efficiency of the analyzer and would explain the higher slope. Thus, this allows the determination of the analyzer recovery separate from the RO element recovery. Again, as stated previously, discrepancies between indicated silica concentrations are presumed to be due to the greater accuracy and lower limit of detection of Analyzer B.

Figure 6:
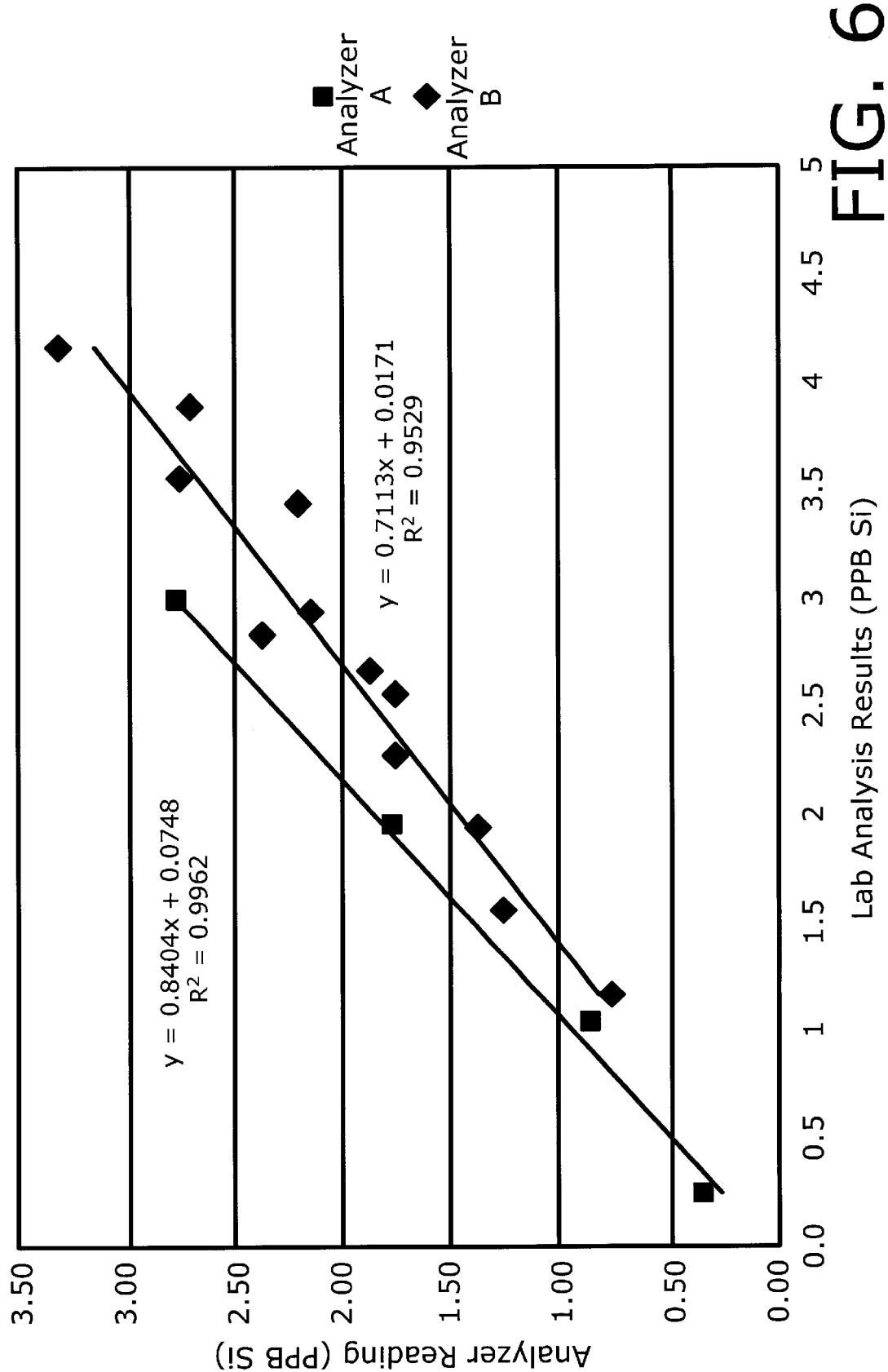
FIG. 6 is a graph of readings from both Analyzer A and Analyzer B in PPB of silica versus the laboratory analysis results in PPB of silica, according to the present invention.

Various samples were taken during several of the test runs and sent to an off-site laboratory for independent analysis. FIG. 6 is a graph of the readings from the analyzers in PPB of silica (y-axis) versus the laboratory analysis results in PPB of silica (x-axis). These axes were chosen so that the slope of the trendline would equal the analyzer recovery. In general, the laboratory analysis yields higher readings of silica in the samples than each of the two analyzers, but the discrepancy between the readings are consistent—as seen by the linear fit. This result confirms the reliability of the UPW concentration technique, as long as the analyzer recovery is taken into account when calculating the true level of silica in the UPW. The Analyzer A appears to read only 84% of the silica actually present in the sample stream while Analyzer B reads approximately 72% of the silica present. Thus, although Analyzer B has a lower zero noise limit, Analyzer A detects more silica in a given sample.

Figure 7:
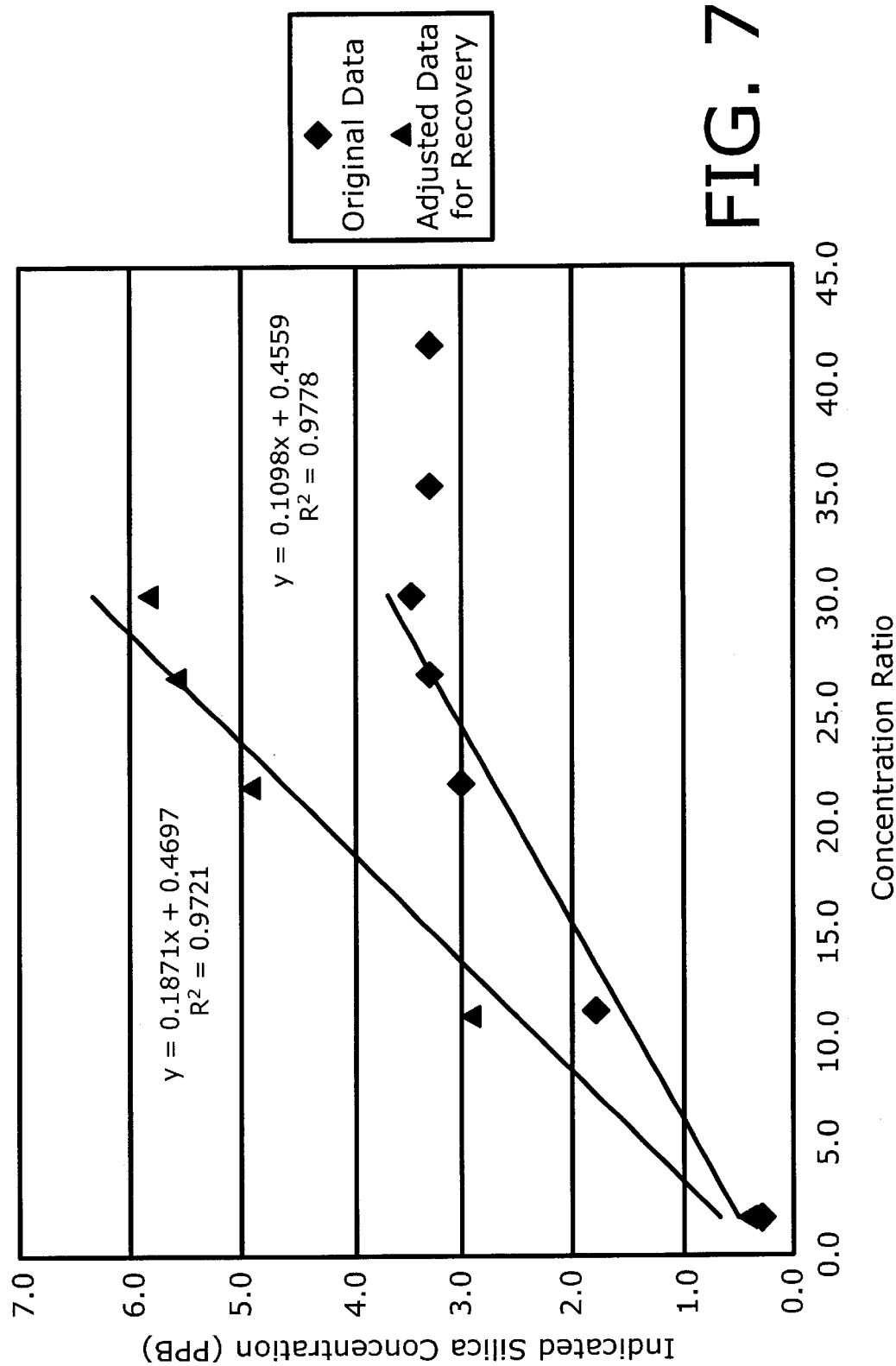
FIG. 7 is a graph of the adjusted and original data for Analyzer A wherein the slope of the trendline for the adjusted data for Analyzer A indicates the true level of silica in the feed stream, according to the present invention.
Figure 8:
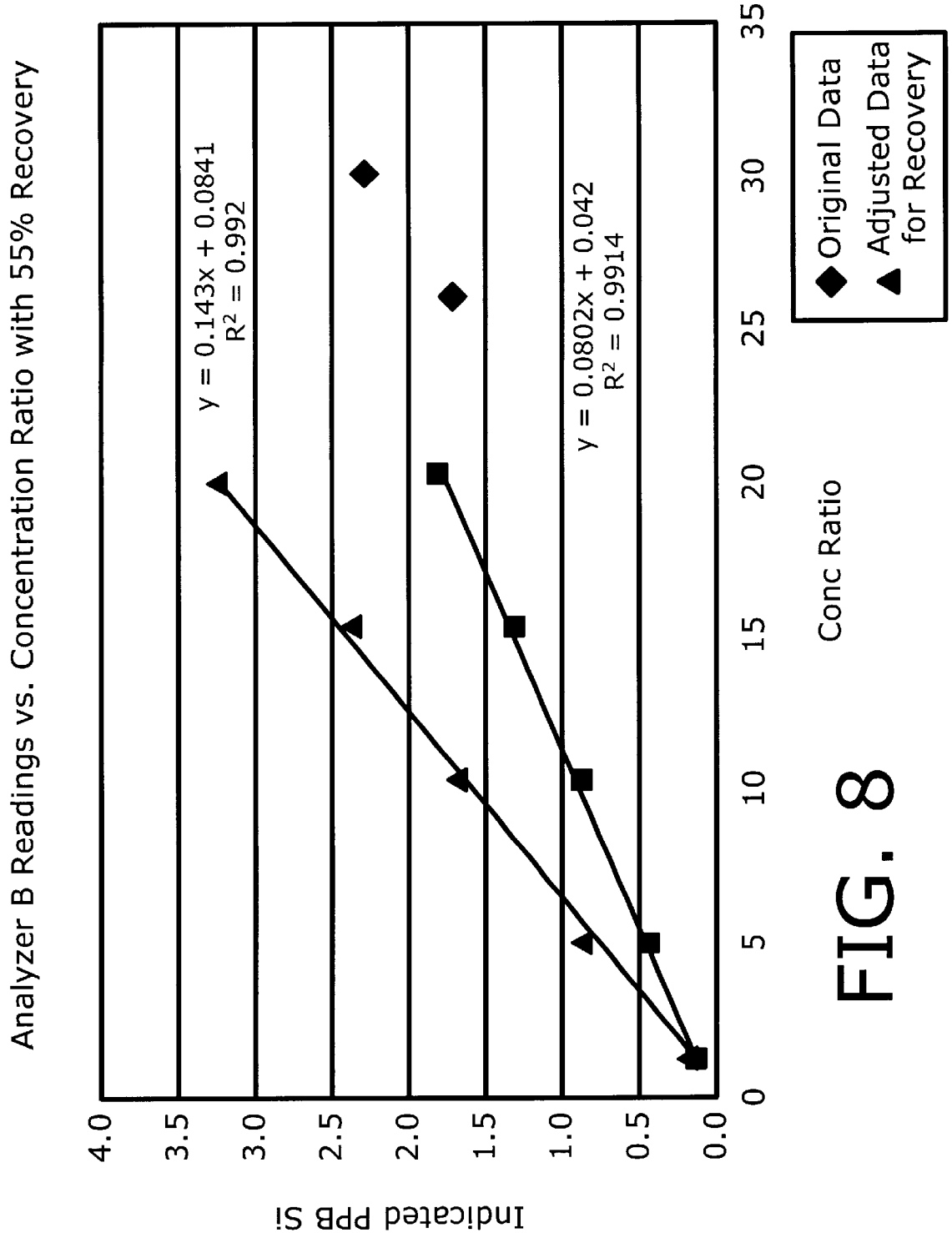
FIG. 8 is a graph of the adjusted and original data for Analyzer B wherein the slope of the trendline for the adjusted data for Analyzer B indicates the true level of silica in the feed stream, according to the present invention.

By using the results of the tests, it is now possible to determine the true level of silica in the UPW. First, the indicated silica concentration (PPB) data from FIG. 3 was adjusted to account for the separate recovery on the two analyzers. Thus, for Analyzer A, each data point was divided by 62% and for Analyzer B, each data point was divided by 55%. The adjusted indicated silica concentration (PPB) data points were then plotted again versus concentration ratio. FIG. 7 is a graph of the adjusted and original data for Analyzer A and FIG. 8 is a graph of the adjusted and original data for Analyzer B. The resulting slope of the new trendline for the adjusted data for Analyzer A and B indicates the true level of silica in the feed stream. As seen, Analyzer A yields a measurement of 0.19 PPB silica for the tested UPW stream and Analyzer B obtains a calculation of 0.14 PPB silica for the tested UPW stream. However, the zero noise level of Analyzer A is about 0.7 PPB and the zero noise level of Analyzer B is about 0.2 PPB. Thus, the UPW concentrator technique has allowed the true silica level to be determined with the same analyzers that would have previously only reading their own noise in on-line monitoring without the UPW concentrator.

Next, the lower detection limit of the analyzers was calculated to determine the improvement ratio of the technique over conventional on-line monitoring without the UPW concentrator. The RO product water stream can be used as a zero standard and allows the instrument zero to be quantified, as will he discussed with FIGS. 8 and 9. For on-line instrumentation with many analytical results, the lower detection limit can be regarded as a signal shift of three times the instrument's standard deviation above the zero baseline. The standard deviation was determined using statistically techniques well known in the art. Using Analyzer A (standard deviation of 0.02) as an example:

3×0.02=0.06 PPB (Analyzer A's lower detection limit)

Arbitrarily choosing a 20×-concentration ratio and Analyzer A's 62% recovery (as discussed previously), the detection limit of Analyzer A with the UPW concentrator is:

0.06 PPB/20/0.62=0.005 PPB (Lower detection limit with the UPW concentrator)

The current lower detection limit of off-site laboratories is 0.1 PPB. Thus, the resulting analytical improvement of the present invention over laboratory analysis is:

0.1/0.005=20 (factor of improvement over an off-site laboratory)

Analyzer A has a lower detection limit of 0.7 PPB (i.e., the zero noise limit). Thus, the resulting analytical improvement of the present invention over using Analyzer A without the UPW concentrator is:

0.7/0.005=140 (factor of improvement over Analyzer without UPW concentrator)

Figure 9:
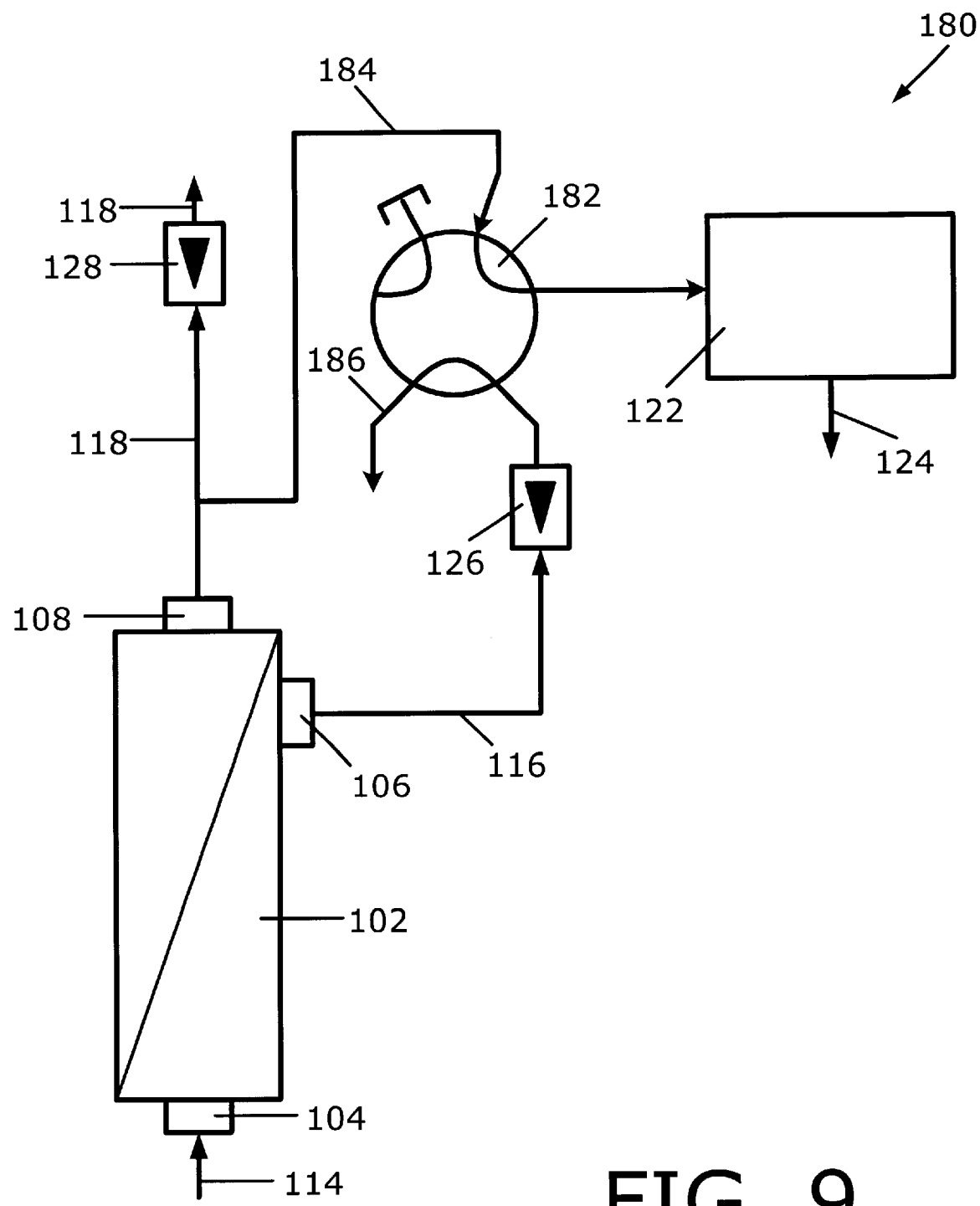
FIGS. 9 and 10 are schematic of an on-line contaminant concentration apparatus, according to the present invention.
Figure 10:
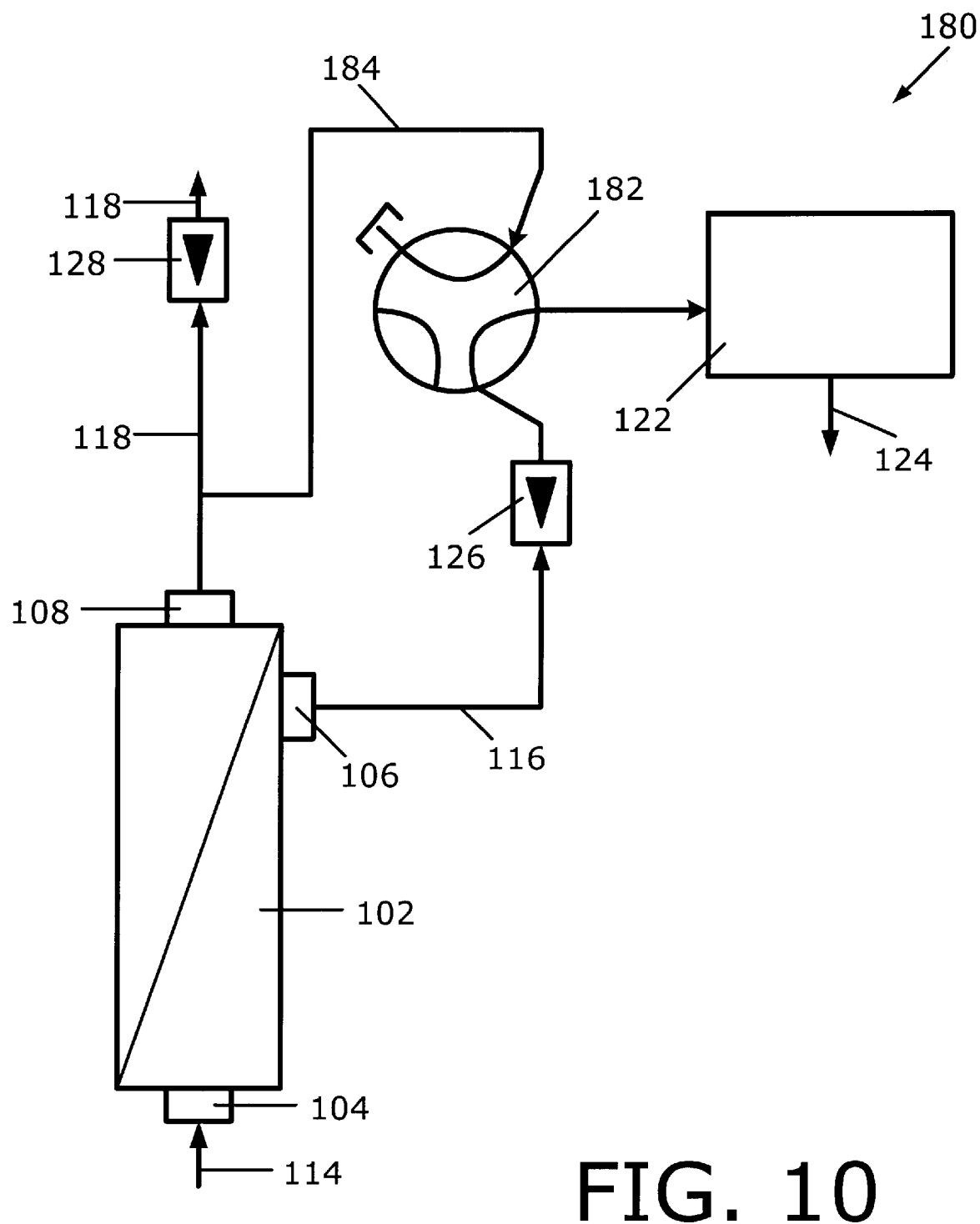

FIGS. 9 and 10 illustrate an embodiment of an on-line contaminant concentration apparatus 180 of the present invention. When such an on-line contaminant concentration apparatus 180 is installed, its zero noise level needs to be determined. The zero noise level is determined using a four-way selector valve 182 to feed at least a portion of the product stream 118, as a zero stream 184, to the analyzer 122, as shown in FIG. 9. The concentrate stream 116 is merely routed though the four-way selector valve 182 and discarded as waste stream 186. The product stream 118 can be used as the zero stream 184 (i.e., zero contamination level water) to qualify the analyzer 122, because it is cleaner than the UPW being tested.

The zero level changes each time the analyzer reagents and standards are replenished, thus this calibration must be determined each time the reagents are changed. A silica study similar to the aforementioned may then be carried out to determine the particular recovery percentage of the RO unit and analyzer. The silica study does not need to be completed each time reagents are replenished since data from similar tests may be used.

Once the zero noise level is established. on-line monitoring can then begin by shifting the four-way selector valve 182 to block the flow of the zero stream 184 and allow the flow of concentrate stream 116 to the analyzer 122, as shown in FIG. 10. Preferably, on-line monitoring should be performed using a concentration ratio equal to or less than 20× for optional results. The indicated level of silica can then be entered into the following formula to determine the true level of silica:

{(Silica level as indicated by analyzer)−(analyzer zero reading)}(analyzer specific efficiency)/(concentration ratio)

Thus, the UPW concentrator technique allows for a method of reliably monitoring silica levels on-line in UPW, even level less than 0.1 PPB and with a lower detection limit in the single digit parts per trillion. This will permit accurate on-line monitoring of silica and/or other contaminants to more effective monitor UPW systems and make necessary adjustments.

It is, of course, understood that the UPW concentrator technique is not limited to silica. It has also been extended to other contaminants and other monitored indicators. The technique has been successful with fluoride, chloride, total silica, dissolved silica, boron, as well as resistivity tracking.

Having thus described in detail embodiments of the present invention, it is understood that the invention defined by the appended claims is not to be limited by particular details set forth in the above description, as many apparent variations thereof are possible without departing from the spirit scope thereof.

What is claimed is:

1. A contaminant analysis method, comprising:
    delivering a feed stream having a contaminant of interest to a filtering device;
    separating said feed stream into a product stream and a concentrate stream with said filtering device;
    delivering said concentrate stream to a contaminant analyzing device;
    determining a zero reading for said contaminant analyzing device, comprising:
        delivering said feed stream having said contaminant of interest to said filtering device;
        separating said feed stream into a product stream and a concentrate stream with said filtering device;
        delivering said product stream to said contaminant analyzing device;
        determining an indicated concentration of said contaminant of interest within said product stream with said contaminant analyzing device; and
        calculating said zero reading of said contaminant analyzing device from said indicated concentration;
    determining a concentration of said contaminant of interest within said concentrate stream with said contaminant analyzing device; and
    calculating a concentration of said contaminant of interest within said feed stream.

2. The method of claim 1, wherein said delivering said feed stream having said contaminant of interest to said filtering device comprises delivering said feed stream having said contaminant of interest to a filtering device selected from the group consisting of a reverse osmosis device, a nanofiltration device, and an ultrafiltration device.

3. The method of claim 1, wherein said separating said feed stream into said product stream and said concentrate stream with said filtering device comprises separating said feed stream into said product stream and said concentrate stream, wherein a concentration ratio between said feed stream and said concentrate stream is equal to or less than about 20.

4. The method of claim 1, wherein calculating said concentration of said contaminant of interest within said feed stream comprises calculating said concentration based on said concentration of said contaminant of interest within said concentrate stream, said zero reading of said contaminant analyzing device, a known specific efficiency of said contaminant analyzing device, and a concentration ratio between said concentrate stream and said feed stream.

* * * * *

UNITED STATES PATENT AND TRADEMARK OFFICE
CERTIFICATE OF CORRECTION

PATENT NO. : 6,420,185 B1
DATED : July 16, 2002
INVENTOR(S) : Carr

It is certified that error appears in the above-identified patent and that said Letters Patent is hereby corrected as shown below:

Column 5,
Line 66, before "substantially", delete "to".

Column 6,
Line 67, delete "he", insert -- be --.

Signed and Sealed this

Twenty-fifth Day of February, 2003

JAMES E. ROGAN
*Director of the United States Patent and Trademark Office*